United States Patent
Kesling

(10) Patent No.: US 8,925,719 B2
(45) Date of Patent: Jan. 6, 2015

(54) PACKAGE FOR PREPASTED BRACKETS

(71) Applicant: TP Orthodontics, Inc., LaPorte, IN (US)

(72) Inventor: Andrew C. Kesling, Lakeside, MI (US)

(73) Assignee: TP Orthodontics, Inc., Laporte, IN (US)

(*) Notice: Subject to any disclaimer, the term of this patent is extended or adjusted under 35 U.S.C. 154(b) by 21 days.

(21) Appl. No.: 13/828,527

(22) Filed: Mar. 14, 2013

(65) Prior Publication Data

US 2014/0299501 A1 Oct. 9, 2014

(51) Int. Cl.
*A61B 19/02* (2006.01)
*B65D 5/50* (2006.01)

(52) U.S. Cl.
CPC .................... *B65D 5/5002* (2013.01)
USPC ......................... 206/63.5; 206/369

(58) Field of Classification Search
USPC ............ 206/63.5, 368, 369; 433/8, 9
See application file for complete search history.

(56) References Cited

U.S. PATENT DOCUMENTS

| | | | |
|---|---|---|---|
| 4,204,325 A | 5/1980 | Kaelble | |
| 4,948,367 A | 8/1990 | Haas | |
| 4,978,007 A | 12/1990 | Jacobs et al. | |
| 4,979,611 A | 12/1990 | Bolliger et al. | |
| 5,172,809 A | 12/1992 | Jacobs et al. | |
| 5,183,403 A | 2/1993 | Masuhara et al. | |
| 5,221,202 A | 6/1993 | James | |
| 5,328,363 A | 7/1994 | Chester et al. | |
| 5,348,154 A | 9/1994 | Jacobs et al. | |
| 5,354,199 A | 10/1994 | Jacobs et al. | |
| 5,429,229 A | 7/1995 | Chester et al. | |
| 5,538,129 A | 7/1996 | Chester et al. | |
| 5,575,645 A | 11/1996 | Jacobs et al. | |
| 5,636,736 A | 6/1997 | Jacobs et al. | |
| 5,759,028 A | 6/1998 | Bozman | |
| 5,762,192 A | 6/1998 | Jacobs et al. | |
| 5,827,058 A | 10/1998 | Kelly et al. | |
| 6,089,861 A | 7/2000 | Kelly et al. | |
| 6,183,249 B1 | 2/2001 | Brennan et al. | |
| 6,482,003 B2 | 11/2002 | Dixon et al. | |
| 6,786,720 B1 | 9/2004 | Kesling et al. | |
| 6,834,761 B1 | 12/2004 | Kesling | |
| 6,843,370 B2 | 1/2005 | Tuneberg | |
| 6,960,079 B2 | 11/2005 | Brennan et al. | |
| 7,381,053 B2 | 6/2008 | Tuneberg | |
| 7,469,783 B2 | 12/2008 | Rose, Sr. | |
| 7,726,470 B2 | 6/2010 | Cinader, Jr. et al. | |
| 2005/0016884 A1 | 1/2005 | Stout et al. | |
| 2013/0075282 A1* | 3/2013 | Cinader et al. | 206/63.5 |

* cited by examiner

*Primary Examiner* — Bryon Gehman
(74) *Attorney, Agent, or Firm* — Cook Alex Ltd.

(57) ABSTRACT

A package for prepasted brackets mountable on the teeth of a patient wherein the bracket is mounted in a pod and is removable from the pod with adhesive on the back of the bracket so it can be directly placed in position on the tooth of a patient. The bracket includes a body and a base and a layer of light curable or otherwise curable polymer resin on the base which is later curable by use of light energy or otherwise. The package includes a carrier for the brackets and is enclosed by a flap over the top of the pod and held in place on supports or tabs extending upwardly from the bottom of the pod to prevent the polymer resin on the base from engaging the bottom of the pod. Stabilizing structure is provided in the pod to inhibit shifting of brackets during shipment.

17 Claims, 5 Drawing Sheets

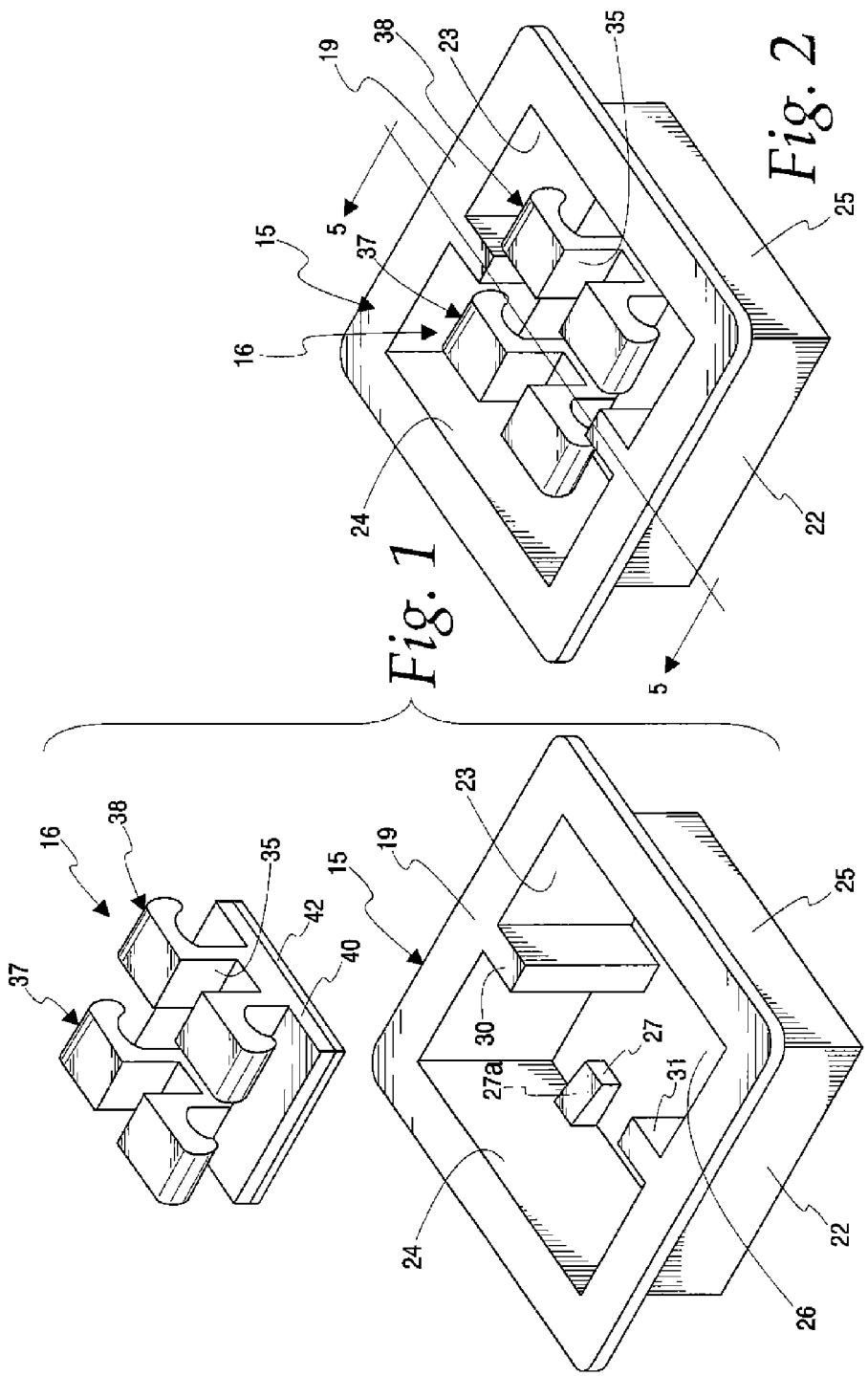

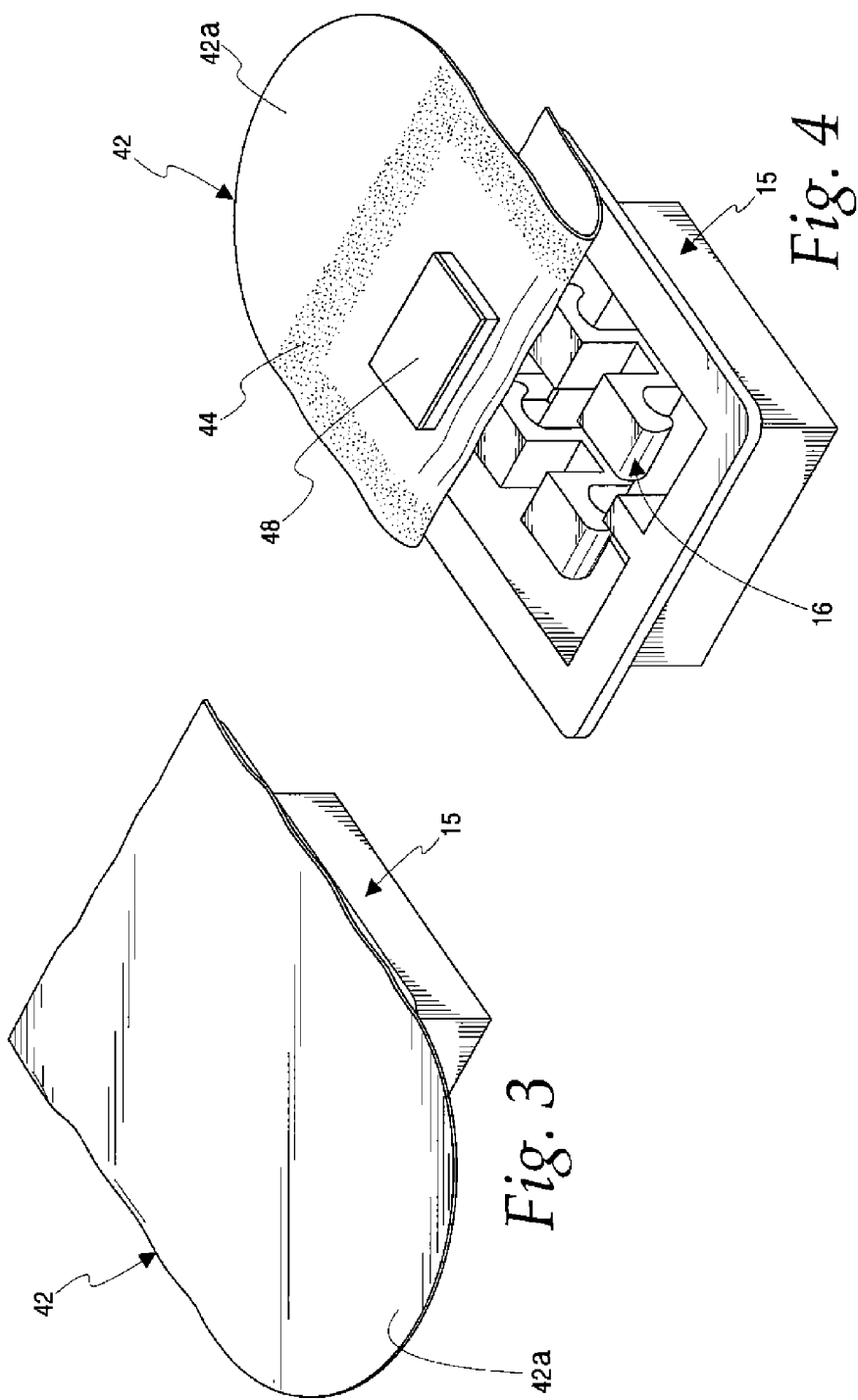

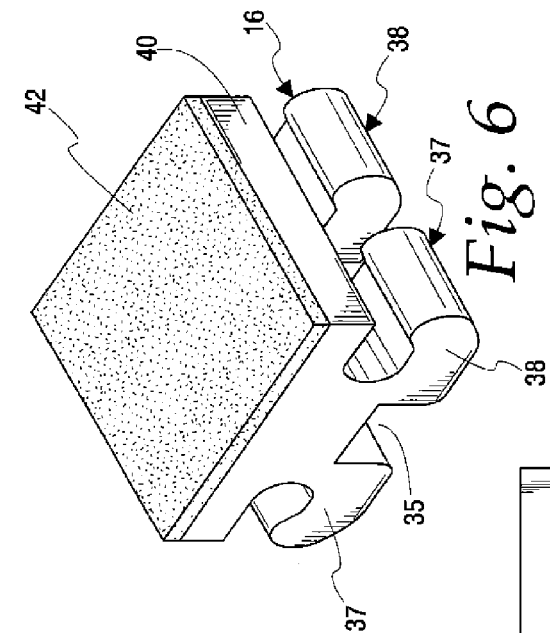
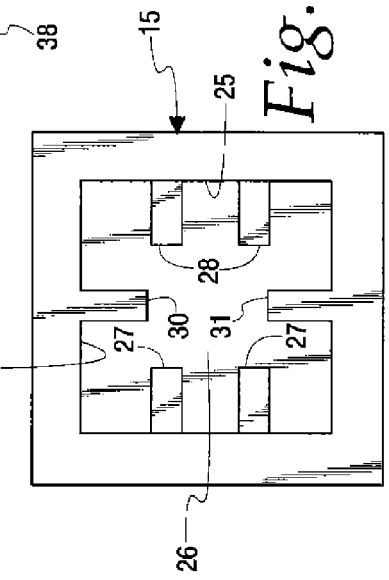
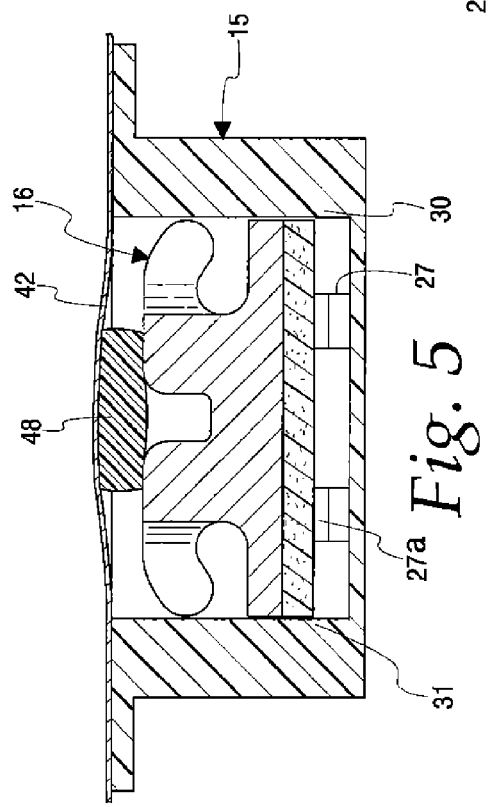
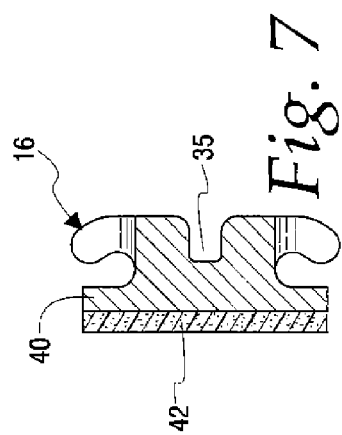

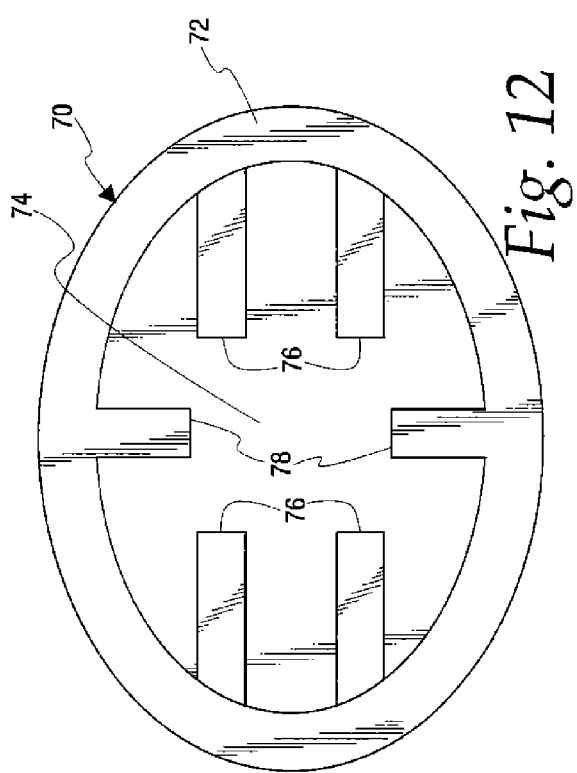
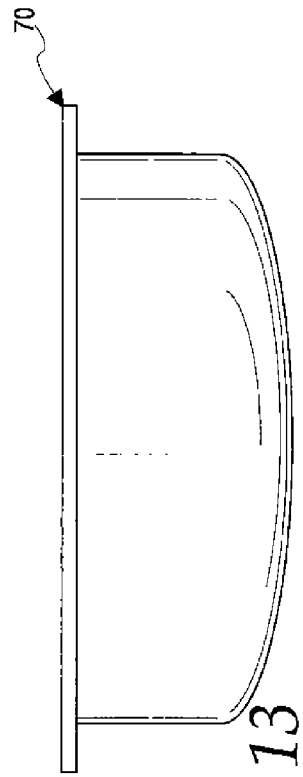
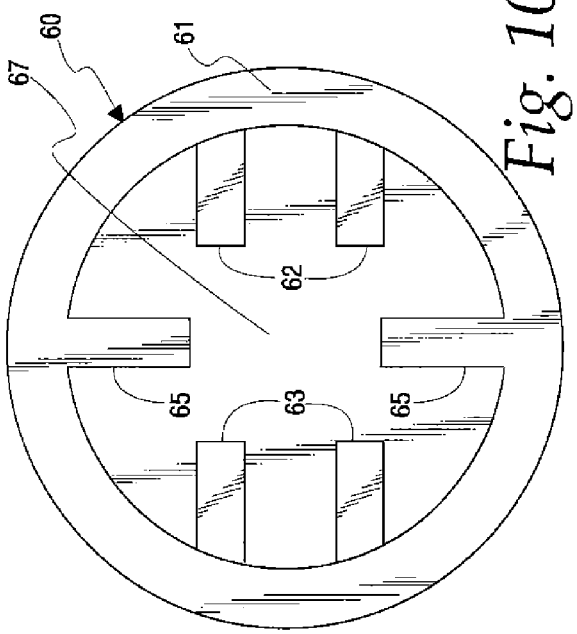
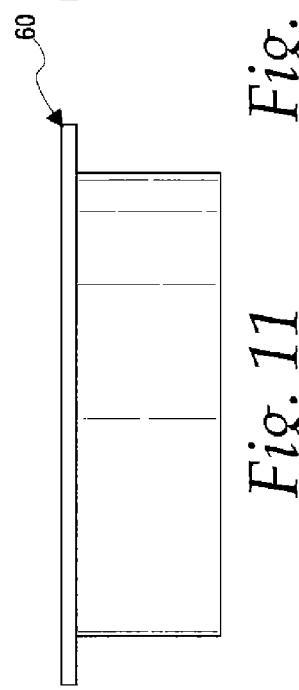

PACKAGE FOR PREPASTED BRACKETS

TECHNICAL FIELD

This invention relates to a new and improved package for prepasted orthodontic appliances and particularly prepasted orthodontic brackets to facilitate shipping of the bracket to a user. The base of such a prepasted bracket includes a layer of uncured bonding material for bonding the bracket to a tooth. The package includes a carrier having one or more pods or compartments, each of which is capable of receiving a prepasted bracket wherein the prepasted bracket is inserted into the pod and resting on tabs upstanding from the base of the pod to prevent the prepasted base from engaging the bottom of the pod. The pod also includes stabilizing tabs extending for maintaining the stability of the bracket during shipping. A flap is provided over the top of the open end of the pod and includes a soft foam element that engages the top of the pod to retain the bracket in position in the pod during the shipment.

BACKGROUND OF THE INVENTION

Heretofore it has been well known to provide carriers with pods for shipping of prepasted brackets such as shown in U.S. Pat. No. 4,978,007 and particularly in FIGS. 9 and 11. The embodiment in FIG. 9 shows the prepasted bracket engaging the bottom of the pod while the embodiment of FIG. 11 shows the prepasted bracket having an alignment device or a jig connected to the bracket to suspend the bracket above the base of the pod so that the adhesive on the back of the bracket does not touch the bottom of the pod. Other prior art patents showing the packaging of a prepasted bracket in a pod include U.S. Pat. Nos. 4,979,611; 5,221,202; 5,328,363; 5,348,154; 5,538,129; 5,762,192; 6,960,079; 7,381,053; and 7,726,470.

With respect to prior known carriers with pods wherein the prepasted bracket engages the bottom of the pod it is always possible to leave a portion of the bonding material in the pod when removing the bracket from the pod and in those cases insufficient bonding material is left on the bracket base to properly bond an appliance to the tooth of a patient.

With respect to carriers having pods where the bracket is supported and suspended from the bottom by means of a jig or an alignment device, there are many clinicians that do not like to have a jig mounted on the bracket when transferring the bracket from a pod to a tooth. It is preferred to just have the bracket jigless which would facilitate speed of mounting the bracket on a tooth and not having to remove the jig from the bracket once it is on a tooth. Sometimes that becomes an issue relative to the proper placement of a bracket on a tooth. Particularly, when the adhesive is uncured.

It is also been known to provide a pod where the bracket is spaced from the very bottom of the pod by virtue of upstanding ridges as shown in U.S. Pat. No. 5,221,202, but this pod is objectionable inasmuch as it does not include stabilizing tabs within the pod in order to assist in preventing the bracket from moving along the projections and disturbing the bonding material and the base of the appliance.

SUMMARY OF THE INVENTION

The packaging for prepasted brackets in accordance with the present invention includes a carrier having one or more pods formed to receive a prepasted appliance and particularly a bracket, and a cover in the form of a flap that can enclose the pod and maintain the bracket in substantially the same position during shipping in order to prevent the movement of bonding material on the base of the bracket and loss of bonding material which could later diminish the bonding strength on a tooth. Accordingly, the packaging pod of the present invention protects prepasted orthodontic appliances having an uncured layer of light curable adhesive on the base during shipment from the manufacturer to the user. It should also be appreciated that the uncured adhesive may be of a type that is chemically or thermally curable for bonding the appliances to hard surfaces such as teeth.

Any suitable light curable polymer resin or bonding adhesive may be used on the appliances such as the Python Light Cured Adhesive sold by TP Orthodontics, Inc. of LaPorte, Ind. Python is a trademark owned by TP Orthodontics, Inc. A suitable activator curable-type of adhesive would be the Python One Step Adhesive or the Right On No Mix Adhesive sold by TP Orthodontics, Inc. Python One Step and Right On are trademarks owned by TP Orthodontics, Inc. Accordingly, a reference to a polymer resin as a bonding adhesive in this application is intended to relate to any suitable light, heat or chemically curable adhesive for bonding appliances to teeth.

The pod of the present invention is incorporated in a carrier that may support one or more pods. A cover member is associated with each pod in order to close the pod after a prepasted appliance is inserted into the pod. The carrier and cover and the pod are all preferably of an opaque material so as to prevent light energy or actinic radiation from entering the pod during the time the prepasted appliance is shipped to a user and curing the light curable adhesive. Within the pod are tabs upstanding from the bottom of the pod to support the bracket above the bottom of the pod and engage a small area of the uncured adhesive on the base of the bracket. The upper bracket engaging surfaces of the pods are preferably tapered downwardly to the center of the pod to center the position of the bracket in the pod and to accommodate brackets of different widths. Other upstanding tabs are provided along opposite walls of the pod engaging edges of a bracket in order to provide stability for the appliance and prevent it from shifting during shipment. While the pod as viewed from the top may be rectangular or square in shape, it should be appreciated that it could be circular or oval shaped as long as it is sized so that a prepasted appliance can be inserted into the pod.

Once the prepasted bracket or appliance is inserted into the pod and resting against the upstanding tabs from the bottom of the pod, a cover member of flexible material is placed over the open end of the pod and suitably adhesively secured around its edges to the carrier in which the pod is located. A tab is provided on one end of the flap or cover in order to facilitate gripping the flap and opening and closing the cover. The other end of the cover member is preferably permanently attached by adhesive or otherwise to be secured to the carrier. The adhesive used to close the cover around the pod opening is preferably a re-positionable type that allows the cover to be opened and/or closed without loss of adhesive power to maintain the cover in place.

The package of the present invention including the carrier with the one or more pods formed, is user friendly to the orthodontic practitioner designed to have prepasted appliances for use in the orthodontic treatment of patients. It would be appreciated that the light cured adhesive on a prepasted bracket is tacky and therefore will stick to the surface of a tooth, and when properly positioned, a curing light can be applied to then cure the adhesive and secure the appliance to a tooth.

BRIEF DESCRIPTION OF THE DRAWINGS

FIG. 1 is an enlarged perspective view of a pod and bracket according to the invention showing a bracket removed from the pod and at an elevated position above the pod;

FIG. 2 is an enlarged perspective view of the pod according to FIG. 1 with the bracket inserted into the pod;

FIG. 3 is an enlarged perspective view of a pod according to the invention wherein a cover is provided and in closed position for enclosing the pod and sealing the bracket in the pod for shipment;

FIG. 4 is an enlarged perspective view similar to FIG. 3 with the cover pulled back to show the contents of the pod and where a bracket is mounted therein;

FIG. 5 is an enlarged cross sectional view taking substantially along line 5-5 of FIG. 2;

FIG. 6 is an enlarged bottom perspective view of a bracket wherein the adhesive layer is partially cut away to show its arrangement on the base of the bracket;

FIG. 7 is an enlarged side elevational cross sectional view of the bracket of FIG. 5;

FIG. 8 is an enlarged top plan view of the pod as shown in FIGS. 1 and 2;

FIG. 10 is an enlarged top plan view of a modified pod according to the invention wherein the pod is circular in shape;

FIG. 11 is an enlarged elevational view of the pod of FIG. 10;

FIG. 12 is an enlarged top plan view of another modified pod according to the invention wherein the pod is oval in shape; and FIG. 13 is an enlarged elevational view of the pod of FIG. 12.

DETAILED DESCRIPTION OF THE INVENTION

Figure 9:
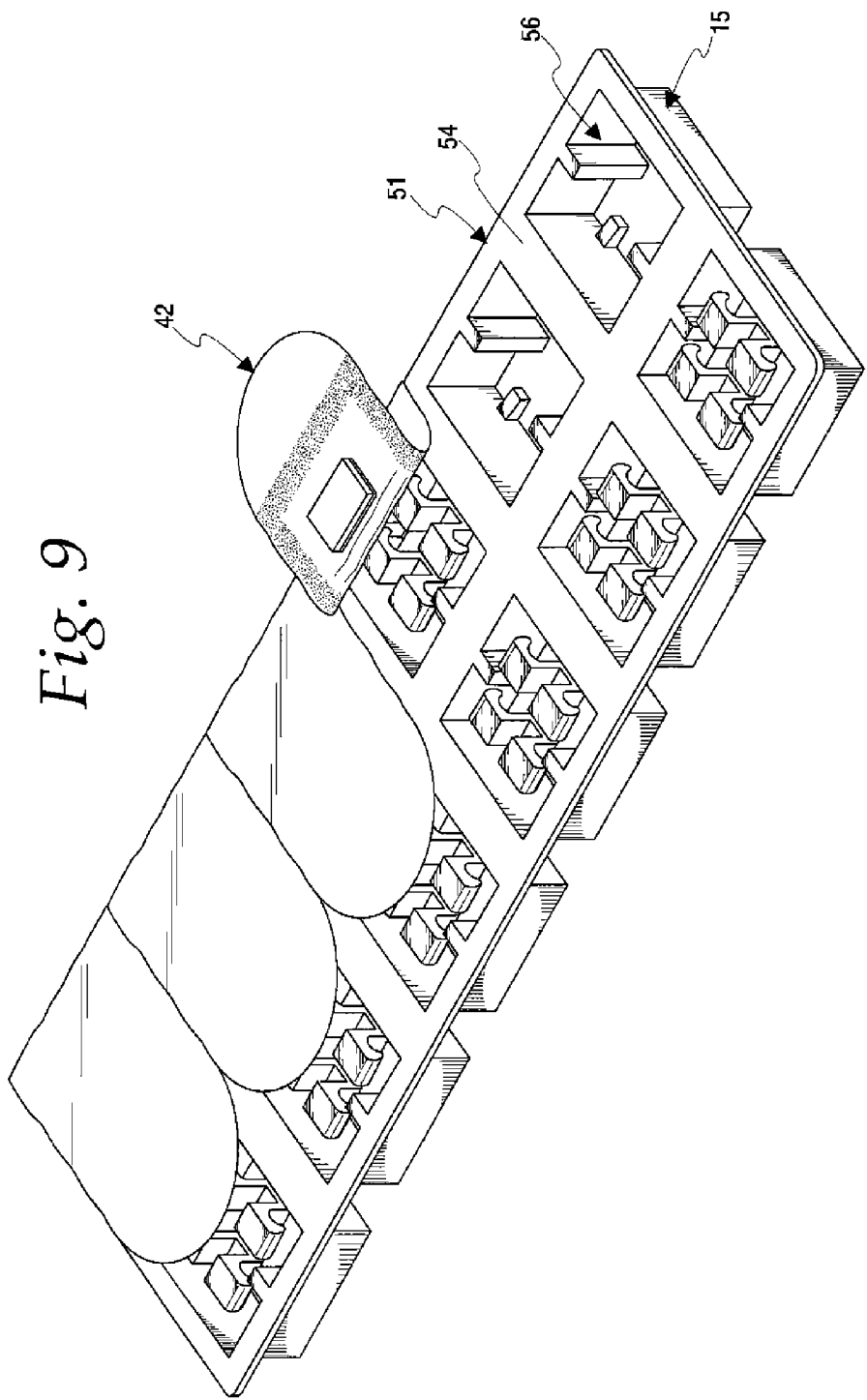
FIG. 9 is an enlarged perspective view of a carrier having a plurality of pods therein for carrying a plurality of brackets with covers shown over some of the pods in closed position and one cover stripped back from the pod to open the pod for allowing the bracket to be inserted in or removed from the pod.

The package of the invention generally includes a carrier having a pod within which a compartment is provided and for which a prepasted bracket may be inserted into position as will be more clearly understood and particularly where the bracket is one having uncured adhesive on the base which is protected against loss of adhesive and curing during shipping.

The carrier may be provided for only a single pod or compartment or a plurality of pods. The embodiment shown in FIGS. 1-8 shows use of a single pod on a carrier. A plurality of pods may be provided on a carrier as seen in FIG. 9 for shipping a number of brackets as a system for a patient.

The pod as shown in FIGS. 1 to 4 is rectangular or square in shape on a carrier and showing the compartment into which a bracket may be received;

The pod may be made of any suitable material such as a plastic or resinous material such as a suitable polystyrene that may be easily shaped by molding, thermoforming or the like into the desired shape.

Although the carrier and pod structure as shown in FIGS. 1 to 4 is only square or rectangular in shape it may be circularly shaped as shown by the embodiment in FIGS. 10 and 11, or oval in shape as shown by the embodiment in FIGS. 12 and 13, or otherwise geometrically shaped to form a space into which a prepasted bracket may be received.

It will be understood herein that a prepasted bracket is one having a layer of uncured adhesive or bonding material on the base which may thereafter be cured depending upon the type of bonding material used. If it is a light curable material as normally provided for these type of brackets, it can be cured by subjecting the adhesive to a curing light. If it is a chemically curable material it may be subjected to the use of a certain chemical in order to cause the layer to cure.

Referring now particularly to FIGS. 1 and 2, the container for a prepasted bracket is shown as being rectangular or square in shape and is generally indicated by the numeral 15 and it is formed for receiving a prepasted bracket which is generally indicated by the numeral 16.

The container includes a carrier 19 which forms a flat surface around the top opening of the pod. Opposed upstanding walls 22 and 23 and also opposing upstanding walls 24 and 25 extending at right angles to the walls 22 and 23 extend downwardly from the carrier to a bottom wall 26.

It will be understood that the pod, which is generally indicated by the numeral 15, is sized and internally constructed to receive brackets of varying widths. A bracket may be easily inserted into and removed from the pod by a suitable tool.

The inside of the pod includes vertically extending tabs or supports 27 and 28 upstanding from the bottom wall 26 and attached to walls 24 and 25 and on which the bracket rests when in the pod and include tapered upper bracket engaging surfaces 27a and 28a. The upper or tapered bracket engaging surfaces of these tabs are downwardly inclined toward the center of the pod so that the pod can receive brackets of various widths. Further the tapered surfaces tend to center a bracket in the pod as it is inserted.

In order to provide stability for the bracket when in the pod, vertically extending tabs 30 and 31 are provided which extend upwardly from the bottom 26 of the pod and inwardly from the side walls 22 and 23 toward each other as particularly shown in FIG. 8. They are sized according to the size of the bracket received in the pod.

The stabilizing tabs 30 and 31 serve to engage a bracket at the upper and lower edges of the bracket base so that the bracket cannot move forward or backward in the pod. While it is still possible for the bracket to move slightly sideways in the pod, the upstanding tabs are sized so that they do not disturb the adhesive layer on the base of the bracket. Moreover it should be appreciated that stabilizing tabs or bars may additionally be provided on the side walls of the pod to engage the sides of the bracket base and assist in keeping the bracket from moving forward and backward in the pod.

While any prepasted bracket may be placed in the pod of the invention for the purpose of illustrating the use of the pod, a standard edgewise bracket 16 is illustrated. This edgewise bracket includes an outwardly facing archwire slot 35 and a pair of tie wings 37 and 38. A base 40 is provided on which the tie wings are mounted and to make the bracket a prepasted bracket a layer of uncured adhesive 42 is provided over the base.

As above mentioned it would be appreciated that any type of bracket with a prepasted base may be shipped in the pod of the invention. For example, it may be a single wing bracket, it may be a triple wing bracket or could be a self-ligating bracket or any other suitable type of bracket where the base is provided with a layer of uncured adhesive. A twin wing bracket is shown in the drawings. Further, it should be appreciated that other prepasted appliances such as a buccal tube may also be provided for shipping in this pod.

Unlike the packaging for the brackets shown in U.S. Pat. No. 7,469,783, wherein a jig is attached to the bracket before it is inserted into the package, it will be understood that with respect to the present invention, there will not be a jig provided with the bracket because many of the orthodontists prefer to have a jig-less bracket when they are mounting a bracket onto a tooth so they do not have to be bothered with removing the jig before finalizing the placement of a bracket on a tooth.

While the pod may be made of any suitable material, it will be understood that it could be suitably molded from a polystyrene plastic or any other suitable plastic. It would be appreciated that the pod will be preferably of opaque material as will be a cover over the open end of the pod in order to preclude light from entering the pod and causing partial or complete curing of a light curable adhesive applied to the bracket base.

Referring to FIGS. 3, 4 and 5, it is seen that the pod in those views is provided with a cover generally designated by the numeral 42 that may be positioned over the pod opening and held in place by repositionable adhesive that is applied preferably to the cover member and which will allow the cover to be lifted and opened in order to allow access to the pod for insertion and/or removal of a bracket in the pod. It will be appreciated the adhesive could be applied on the carrier.

The cover 42 is in closed position in FIGS. 3 and 5 and partially open position in FIG. 4 and the cover also includes the area of repositionable adhesive 44 that will align with the carrier of the pod when in closed position to fully secure the cover in place. Particularly where a light curable adhesive is used on the bracket, it is required that the cover be opaque to light energy that would cause any preliminary curing of the adhesive on the bracket. It will be understood that the cover member will be of flexible material and could be of a suitable plastic or paper that would have the necessary opaqueness to prevent light from entering the interior of the pod and affecting the curing of the adhesive on the base of the bracket.

As seen particularly in FIGS. 3 and 4, the cover member may be permanently attached at its back edge to the top of the pod on the carrier and merely have the repositionable adhesive 44 in the areas where the cover would be engaging the sides and front of the pod carrier. It will be understood the adhesive 44 could alternately be applied to the carrier 19.

A tongue 42a is provided on the cover which would extend beyond the front of the pod so that it could be easily engaged by a tool or by the hand of a person when it is desired to open the cover to provide access to the pod and to close the cover.

Additionally the cover is provided with a foam pad 48 positioned on the underside thereof such that when the cover is in closed position the pad will engage the top surface of the bracket as particularly shown in FIG. 5 to inhibit shifting of the bracket within the pod. The foam pad would be sized and of such a nature to apply slight downward force on the bracket against the tapered supports so that when the bracket is shipped in the pod it will tend to remain in position at all times. The foam pad may be of any suitable structure that will provide a sponginess and have some give to it when the cover is applied to the pod.

Referring now to the embodiment of FIG. 9 where a carrier with multiple pods is provided and some of the pods have covers and one pod has a cover that is partially open. This embodiment, generally indicated by the numeral 51, includes a carrier 54 in which a plurality of pods 56 are aligned in groups of six. Particularly the carrier is all formed together with the pods during the molding process of the unit so that the various pods are included with their upstanding tabs supporting the bracket and upstanding tabs and to stabilize the bracket in position. It is shown that there are two pods that are without any brackets mounted therein and the remainder of the pods that are open are shown with brackets mounted in the pods. Three of the pods have the covers overlying the pods to enclose a bracket within the pod and one pod has a cover that is open to provide access to the pod for removal and/or for insertion of a bracket. It would be appreciated that while this embodiment of FIG. 9 shows a carrier having 12 pods, other carriers may only have two, four, six or any combination number of pods at one time. FIG. 9 is just illustrative of the use of multiple pods on a carrier for handling multiple brackets and particularly where a system is provided on one carrier for a particular patient and all of the brackets are suitably sized and made for particular teeth on a patient according to a system.

It will further be appreciated that the shape of the pod may be other than rectangular or square as shown by the embodiments of FIGS. 10-13. The embodiment of FIGS. 10 and 11 illustrate a pod 60 that is circular in shape but also includes the base mounting tabs 62 and 63 and the stabilizing tabs 65. The upstanding tabs or supports 62, 63 and 65 will provide the same function as in the embodiment of FIGS. 1-8 in allowing a bracket to be inserted into the pod and to be resting on the tabs 62 and 63 and stabilized in position by tabs 65. These tabs are tapered downwardly toward the center of the pod like the embodiment of FIGS. 1-8. Pod 60 also includes a bottom wall 67 and all of the tabs 62, 63 and 65 are mounted on the bottom wall and extend upwardly or are upstanding therefrom.

The pod would be suitably sized, of course, to receive a bracket of a type that is to be shipped and which will be shipped to minimize the effect on the uncured adhesive on the base of the bracket. While not shown, it would be appreciated that a suitable cover will be provided to cover the pod opening and enclose it to completely seal in the bracket and preclude any light from entering that might affect the light curable adhesive on the base of the bracket.

The pod as already mentioned could be made in any suitable shape just so that it would have enough space for a bracket to be inserted and to be supported on its base on upstanding tabs and stabilized by stabilizing tabs.

Another embodiment is shown in FIG. 12 wherein the pod is elliptically or oval shaped and which is generally designated by the numeral 70 and includes also a carrier surface 72, a bottom wall 74, upstanding supporting tabs 76 and upstanding stabilizing tabs 78. The tabs extend upwardly from the bottom wall 74 and are essentially integral with the side wall and have tapered upper surfaces that are engaged by the edges of a bracket like the other embodiments. The side wall of the pod 70 is also oval in shape and extends downwardly to the bottom wall 74. In this embodiment the bottom wall 74 is somewhat rounded at the bottom although it could be flat like the flat wall 67 in the embodiment of the pod 60. Again a suitable cover may be provided of the type shown with the embodiment of FIGS. 1-5 wherein the cover is of a flexible material that can be first held in place by repositionable adhesive on the cover on the carrier portion of the pod and liftable to open the pod for access to insert and/or remove a bracket within the pod.

It will be appreciated that the shape of the pod may be of any suitable type and the round and oval shapes shown in FIGS. 10-13 are merely illustrations of different shapes of pods. The pod must have a compartment into which a bracket may be inserted and tabs for supporting the base of the bracket and also for stabilizing the bracket within the pod. Further the pods shown in FIGS. 10-12 will be suitably molded, preferably of a polystyrene plastic.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

I claim:

1. A package for a prepasted bracket comprising a carrier having a pod within which a bracket may be received,
   wherein the bracket includes an upper side having an archwire slot, a bottom side having a base, opposed edges, and bonding adhesive on the base,
   said pod having a bottom wall and sidewalls extending upwardly from the bottom wall defining an opening into which a bracket may be inserted,
   seating tabs in said pod extending upwardly from said bottom wall on which the bracket can be supported above said bottom wall when inserted into the pod to prevent the bonding adhesive from contacting the bottom wall,
   stabilizing tabs in the pod extending from the sidewalls and engagable with the bracket to prevent movement of the bracket within the pod, and
   a cover attached to the pod and movable between open and closed positions for enclosing the opening when in closed position,
   said cover including a pad extending therefrom into the pod when the cover is in closed position to engage the upper side of the bracket and urge the bracket to engage the seating tabs,
   whereby the bracket is inhibited from shifting in the pod during shipping.

2. The package of claim 1, wherein the seating tabs include upper surfaces that are tapered downwardly from the sidewalls to the center of the pod.

3. The package of claim 1, wherein said pod is rectangular in shape.

4. The package of claim 1, wherein said pod is circular in shape.

5. The package of claim 1, wherein said pod is oval in shape.

6. The package of claim 1, wherein the package is opaque to light curing energy wherein the bonding adhesive is light curable.

7. The package of claim 6, wherein the seating tabs include a plurality of vertically extending tabs.

8. The package of claim 1, wherein the seating tabs include at least one vertically extending tab having an upward surface tapered downwardly toward the center of the pod.

9. The package of claim 1, wherein said stabilizing tabs include at least one vertically extending tab for engaging at least one edge of the bracket.

10. The package of claim 1, wherein said stabilizing tabs include a plurality of vertically extending tabs engaging a plurality of edges of the bracket.

11. The package of claim 1, wherein said cover is of a flexible material hinged at one end to the carrier, and having repositionable adhesive for selectively engaging said carrier to close the opening or to be swung upwardly from the carrier to an open position.

12. The package of claim 11, wherein the material of the cover is opaque to light energy that could cause curing of the adhesive.

13. The package of claim 11, wherein said pad on said cover includes a resilient material to apply a force against the bracket to hold the bracket in seated position against the seating tabs.

14. The package of claim 13, wherein said resilient material is in the form of a soft foam.

15. The package of claim 1, wherein the bonding adhesive is light curable.

16. A package for a prepasted bracket comprising a carrier having a pod or compartment within which a bracket may be received,
    wherein the bracket includes an upper side having an archwire slot, a bottom side having a base, opposed edges, and bonding adhesive on the base,
    said pod having a bottom wall and sidewalls extending upwardly from the bottom wall defining an opening into which a bracket may be inserted,
    spacing means in said pod extending upwardly from said bottom wall defining support surfaces on which the bracket can be supported above said bottom wall when inserted into the pod to prevent the adhesive on the base from contacting the bottom wall, and
    a cover attached to the pod and movable between open and closed positions for enclosing the opening when in closed position,
    said cover including a pad extending therefrom into the pod when the cover is in closed position to engage the upper side of the bracket and urge the bracket to engage against the support surfaces of the spacing means,
    whereby the bracket is inhibited from shifting in the pod during shipping.

17. A packaged orthodontic assembly comprising;
    an orthodontic appliance having a base for attaching to a surface;
    an adhesive extending across as least a portion of the base;
    a carrier for the appliance having a pod into which the appliance may be placed or removed therefrom;
    said pod defined by a bottom wall, and an upstanding wall;
    seating tabs in said pod extending upwardly from said bottom wall on which the appliance can be supported above said bottom wall when inserted into the pod to prevent the bonding adhesive from contacting the bottom wall,
    stabilizing tabs in the pod extending from the sidewalls and engagable with the appliance to prevent movement of the appliance within the pod, and
    a cover attached to the pod and movable between open and closed positions,
    said cover including a pad extending therefrom into the pod when the cover is in closed position to engage the upper side of the appliance and urge the appliance to engage the seating tabs,
    whereby the appliance is inhibited from shifting in the pod during shipping.

* * * * *